(12) United States Patent
Witt

(10) Patent No.: US 10,130,804 B2
(45) Date of Patent: Nov. 20, 2018

(54) SYRINGE—IV ACCESS LOCKING DEVICE

(71) Applicant: Becton, Dickinson and Company, Franklin Lakes, NJ (US)

(72) Inventor: Erik K. Witt, Wyckoff, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 62 days.

(21) Appl. No.: 15/343,545

(22) Filed: Nov. 4, 2016

(65) Prior Publication Data

US 2017/0072181 A1 Mar. 16, 2017

Related U.S. Application Data

(62) Division of application No. 14/198,802, filed on Mar. 6, 2014, now Pat. No. 9,517,330.

(60) Provisional application No. 61/774,673, filed on Mar. 8, 2013.

(51) Int. Cl.
| | | |
|---|---|---|
| A61M 39/10 | (2006.01) |
| A61M 25/06 | (2006.01) |
| A61M 5/31 | (2006.01) |
| A61M 39/02 | (2006.01) |
| A61M 39/06 | (2006.01) |

(52) U.S. Cl.
CPC .... *A61M 39/1011* (2013.01); *A61M 25/0606* (2013.01); *A61M 39/10* (2013.01); *A61M 5/3134* (2013.01); *A61M 39/02* (2013.01); *A61M 2039/062* (2013.01); *A61M 2039/1022* (2013.01); *A61M 2039/1044* (2013.01); *A61M 2039/1094* (2013.01); *A61M 2205/6009* (2013.01); *A61M 2205/6045* (2013.01)

(58) Field of Classification Search
CPC .. A61M 2039/1044; A61M 2039/1094; A61M 2205/6009; A61M 2205/6045; A61M 39/1011
See application file for complete search history.

(56) References Cited

U.S. PATENT DOCUMENTS

| | | | | |
|---|---|---|---|---|
| 3,287,031 | A | * 11/1966 | Simmons | ........... H01R 13/6456 285/27 |
| 4,150,673 | A | 4/1979 | Watt | |
| 4,280,723 | A | 7/1981 | Moldestad | |
| 4,302,137 | A | * 11/1981 | Hart | .................... F16B 23/0069 411/432 |
| 4,619,640 | A | 10/1986 | Potolsky | |

(Continued)

FOREIGN PATENT DOCUMENTS

WO 2011/056888 5/2011

OTHER PUBLICATIONS

PCT International Preliminary Report on Patentability in PCT/US2014/021245, dated Sep. 17, 2015, 8 pages.
(Continued)

*Primary Examiner* — Kami A Bosworth
*Assistant Examiner* — William Carpenter
(74) *Attorney, Agent, or Firm* — Servilla Whitney LLC

(57) ABSTRACT

A safety device is described wherein drug delivery systems and methods involve associating unique keys to patients that prevent the interconnection between a drug delivery device and non-complimentary patient key. Medication in a drug delivery device intended for a patient may only be accessed via a particular unique key associated with the intravenous access device of that patient.

11 Claims, 12 Drawing Sheets

(56) References Cited

U.S. PATENT DOCUMENTS

| | | | |
|---|---|---|---|
| 5,693,027 A | 12/1997 | Hansen | |
| 5,725,511 A | 3/1998 | Urrutia | |
| 5,823,702 A * | 10/1998 | Bynum | F16L 19/005 |
| | | | 403/320 |
| 5,947,937 A | 9/1999 | Urrutia | |
| 5,971,019 A * | 10/1999 | Imai | F16L 37/23 |
| | | | 137/614.04 |
| RE38,204 E | 7/2003 | Kazarian | |
| 7,137,654 B2 | 11/2006 | Segal | |
| 7,163,531 B2 | 1/2007 | Seese | |
| 7,458,615 B2 | 12/2008 | White | |
| 7,520,536 B2 | 4/2009 | Tiberghien | |
| 7,648,481 B2 * | 1/2010 | Geiger | A61M 5/3134 |
| | | | 604/110 |
| 8,043,280 B2 | 10/2011 | Bierman | |
| 9,477,049 B2 * | 10/2016 | Gniadek | G02B 6/3894 |
| 2009/0099552 A1 | 4/2009 | Levy | |
| 2010/0004603 A1 | 1/2010 | Kristensen | |
| 2012/0310205 A1 | 12/2012 | Lee | |

OTHER PUBLICATIONS

PCT International Search Report and Written Opinion in PCT/US2014/021245, dated Sep. 4, 2014, 10 pages.
Extended European Search Report in Appln. No. 17150069.7 dated May 16, 2017, 7 pages.

* cited by examiner

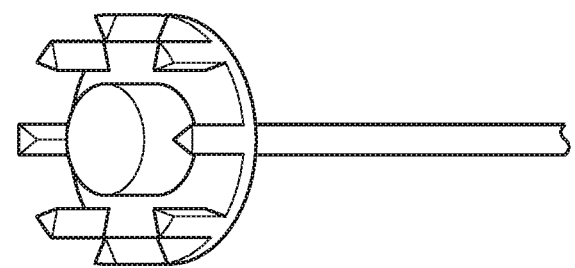
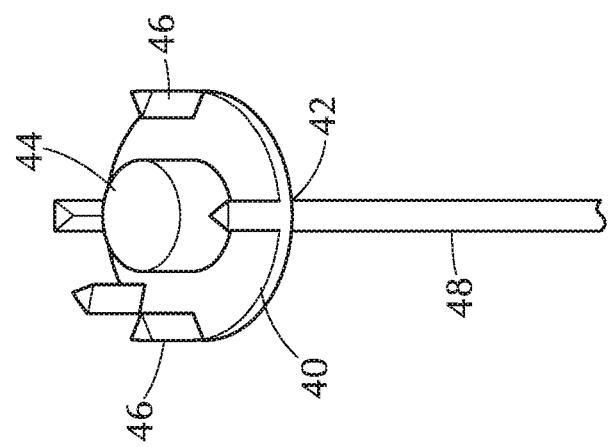
FIG. 2

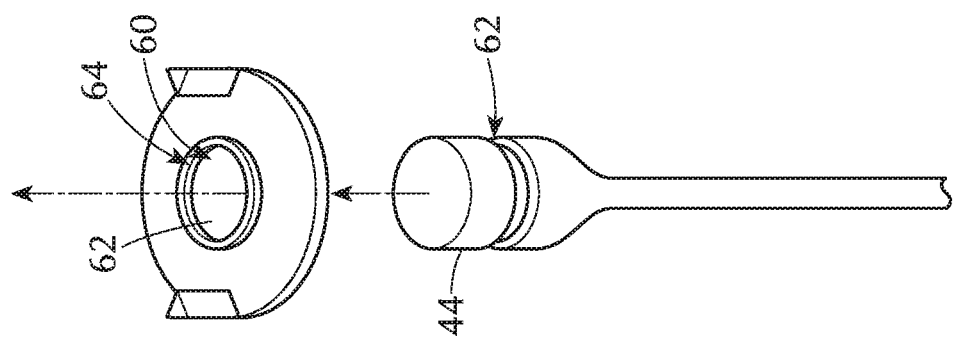
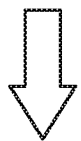
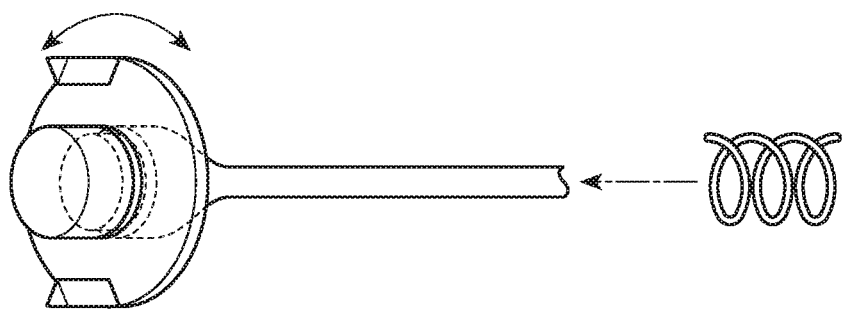
FIG. 3

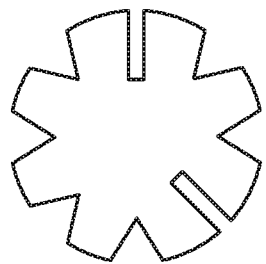
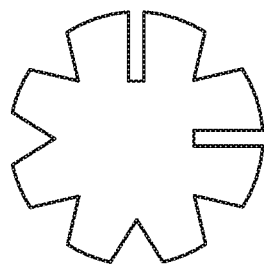
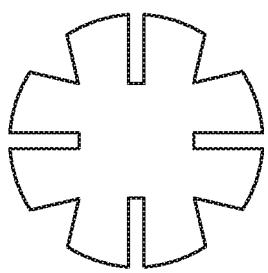
FIG. 4

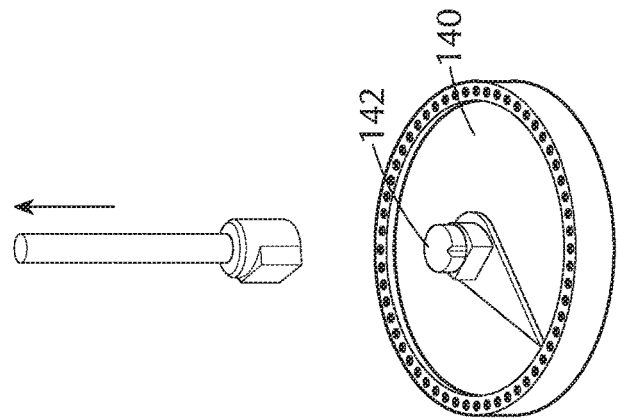
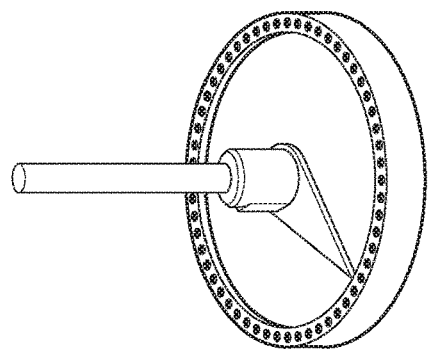
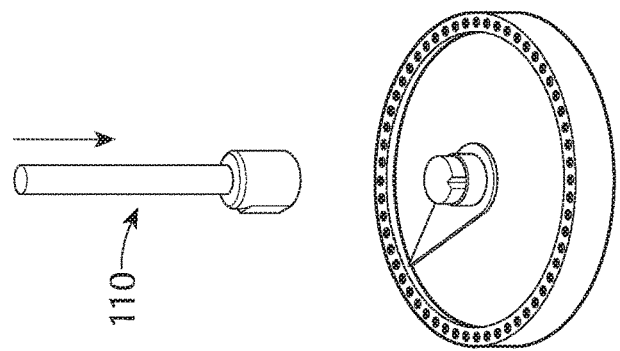
FIG. 6

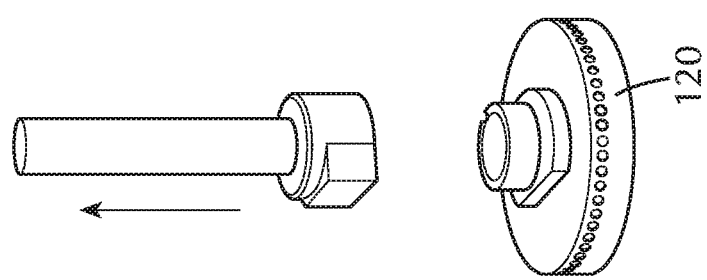
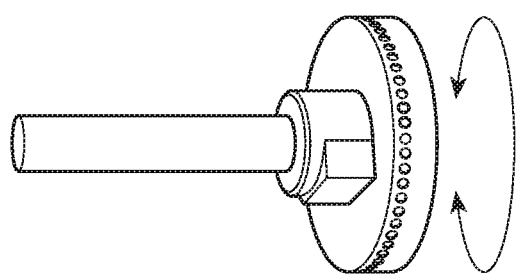
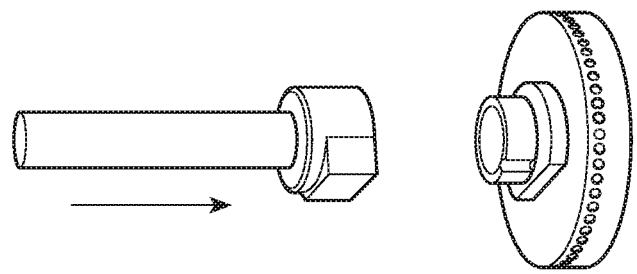
FIG. 7

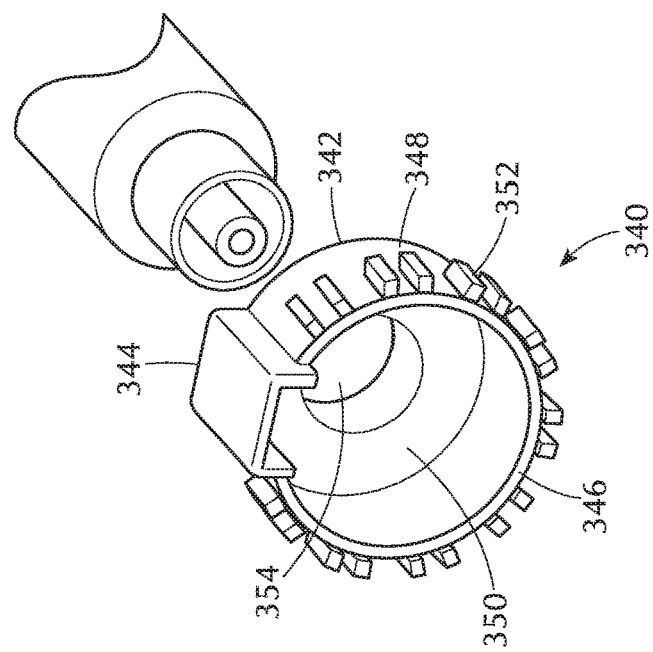
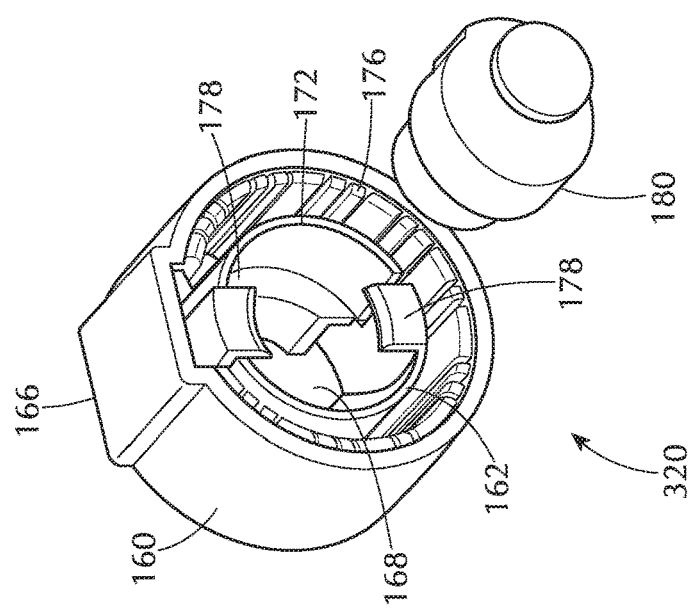
FIG. 9

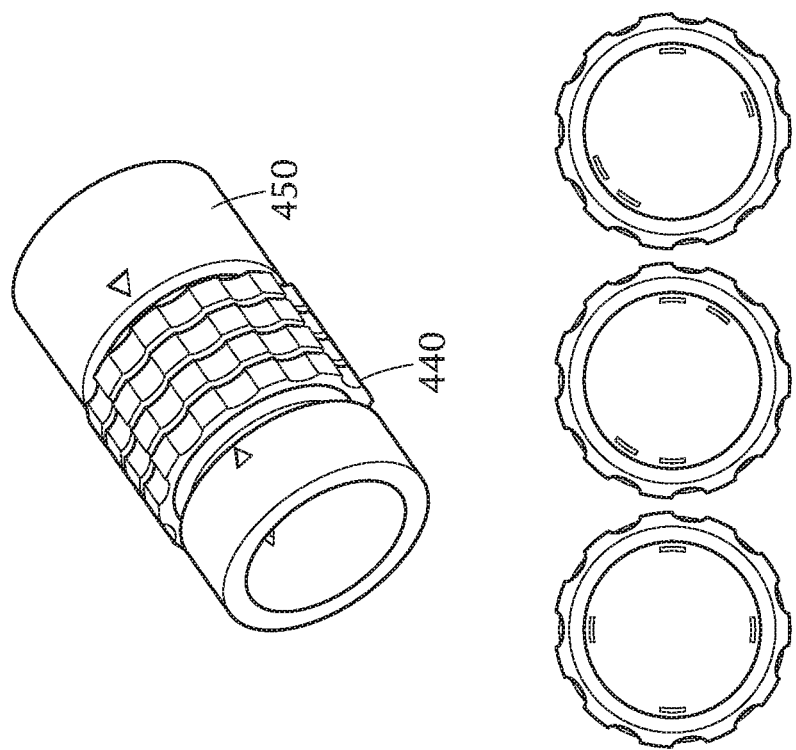
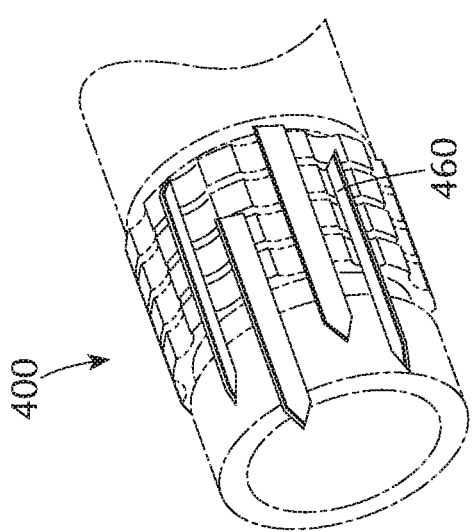
FIG. 12

SYRINGE—IV ACCESS LOCKING DEVICE

CROSS-REFERENCE TO RELATED APPLICATIONS

This application is a divisional of U.S. patent application Ser. No. 14/198,802, filed on Mar. 6, 2014, which claims priority under 35 U.S.C. § 119(e) to U.S. Provisional Application No. 61/774,673, filed Mar. 8, 2013, the disclosures of which are incorporated herein by reference in their entirety.

TECHNICAL FIELD

An aspect of the present invention relates generally to a drug delivery safety device having a locking element attachable a drug delivery device and a keying element attachable to an intravenous access device of a patient. In one embodiment, the locking element has at least one flange with a plurality of configurable cutouts to provide a plurality of notches in a receiving pattern to a keying element attached to a vascular access device having a plurality of configurable projecting tabs to provide a complementary fit with the receiving pattern of the locking element. In another embodiment, the locking element has a keyway that is positioned to correspond with a complementary key tab on the keying element. In yet another embodiment, the locking element has one or more detachable interference ribs that may be selectively configured to form gaps in a pattern to correspond with a complementary pattern of detachable protrusions on the keying element.

BACKGROUND

Misadministration of medication is a significant problem where approximately 59% of all injectable errors occur at administration, and intravenous (IV) drugs account for 75% of injectable preventable adverse drug events in acute care settings. The complexity of parenteral medication administration and increased intolerance of the complications that result from improper medication delivery, create demand for devices that make drug delivery safe and efficient. Safety has been addressed in the market from many perspectives including needles, and fluid containment. A simple solution to help ensure medications are correctly delivered to patients via the parenteral route is not currently addressed.

Different size Luer connectors are passive approaches, but do not provide a unique patient-specific key. Active approaches that require information technology infrastructure such as radio frequency identification (RFID) tags and bar codes address the problem, but these active approaches require a significant investment for their implementation. Further, there is concern that due to the wide adoption of the Luer lock in many applications, drugs can be administered through improper ports. For example, anesthesia injections intended for the spine, IV injections, and gasses can all employ the same connections for delivery.

Thus, there is a need for a passive approach that provides a unique patient-specific key to prevent or reduce the improper administration of parenteral medications.

SUMMARY

One aspect of the present invention pertains to a drug delivery safety device comprising a locking element having a body with a proximal end and a distal end, the proximal end of the locking element being attachable a drug delivery device and the distal end of the locking element having at least one flange with a plurality of mechanically configurable sections to provide a patient specific pattern of receiving openings. The device also comprises a keying element having a proximal end and distal end, the proximal end may be attachable to a vascular access device, and the distal end may have a plurality of mechanically configurable engagement members. The drug delivery device securely connects to the vascular access device when the engagement member of the keying element is configured to provide a complementary fit with the patient specific pattern of receiving openings of the locking element.

In one or more embodiments, the drug delivery device may be a syringe, intravenous catheter connector, IV bag spike, or point of interconnection in an IV administration set. The syringe may have a tip located in the body of the locking element.

In one or more embodiments, the mechanically configurable sections may comprise a plurality of configurable notches. The plurality of configurable notches may incorporate predetermined geometrical shapes and may be located on the periphery of the flange. An end user may configure a selected number of notches to create a locking element to distinguish the route of administration. The route of administration may be parenteral, enteral or anesthesia.

The locking element may have two flanges. The one or more flange may have a circular shape.

In one or more embodiments, an end user may remove, move, rotate, reshape, melt, reposition, uncover, or puncture one or more of the plurality of mechanically configurable sections.

The locking element may be configured to be patient specific, application specific or drug specific. In one or more embodiments, the locking element may also comprise a sensor. The keying element may be rotatable and/or spring-loaded. In one or more embodiments, the keying element may further comprise a sensor. The locking element and keying element may be associated with only one patient or small number of patients of a larger patient population.

The engagement members may comprise removable tab-like projections to identify an individual patient, application or drug type.

In one or more embodiments, the drug delivery safety device may also comprise a visual indicator for drug family identification. The drug delivery safety device may also comprise a master keying element capable of unlocking two or more individualized locking elements.

Another aspect of the present invention pertains to a drug delivery safety device comprising a locking element comprises a housing having a curved-shaped outer sidewall with a flat ledge on a top portion, an inner sidewall having an open central cavity, and a back wall located between the inner and outer sidewalls. The inner sidewall may have a distal end and a proximal end, the distal end may have one or more detenting ribs protruding radially outward around the outer circumference, and the proximal end of the inner sidewall may have one or more inwardly protruding tabs. The device also comprises a needleless IV connector disposed in the open central cavity of the inner sidewall and held between the one or more inwardly protruding tabs of the inner sidewall and a first insert having an open distal end and an open proximal end; a sidewall extending between the open distal end and the open proximal end, the sidewall on the distal end may have more than one detents on an inside circumference of the sidewall protruding radially inward toward the central axis, the one or more detents of the first insert having a complimentary fit with the one or more detenting ribs of the housing when the first insert is place into the housing. A keyway may be cut into the sidewall on the proximal end of the first insert to correspond with an individual patient. A keying element may comprise a housing having a outer sidewall having a curved shape with a flat ledge on a top portion, the outer sidewall having an open distal end and a proximal end having a back wall, an inside surface of the proximal end of the outer sidewall having one or more detents located around the circumference of the inside surface of the proximal end of the outer sidewall protruding radially outward, the back wall may have an open central cavity formed by a second inner wall. The device also comprises a second insert having an open distal end and an open proximal end; a sidewall extending between the open distal end and the open proximal end, the sidewall on the proximal end may have one or more detenting ribs on an outer circumference of the sidewall protruding radially outward, the one or more detenting ribs of the second insert may have a complimentary fit with the one or more detent of the housing when the second insert is place into the housing, a key tab projecting radially inward from the distal end of the second insert toward the central axis. The outer sidewall of the keying element may have a diameter smaller than the outer diameter of the outer sidewall of the locking element to enable the keying element to slide into the locking element when the keyway of the locking element is aligned with the tab projecting radially inward from the distal end of the second insert.

In one or more embodiments, the locking element may be placed on a drug delivery device. The drug delivery device may be a syringe. In one or more embodiments, the keying element may be placed on an intravenous access device. In one or more embodiments, the housing of the locking element may also be imprinted with numerical values assigned to different positions of the keyway. In one or more embodiments, the housing of the keying element may be imprinted with numerical values assigned to different positions of the key tab. The position of the keyway and key tab may be patient specific, specific to a route of administration, or specific to a drug class. In one or more embodiments, the device may further comprise a visual indicator for drug family identification.

Another aspect of the present invention pertains to a drug delivery safety device comprising a locking element comprises a housing having an outer sidewall, an inner sidewall, a back wall located between the inner and outer sidewalls. The outer sidewall may have a curved shape with a flat ledge on a top portion, the inner sidewall creating an open central cavity. The inner sidewall has a distal end and a proximal end. The inside surface of the curved portion of the outer sidewall may have one or more detachable interference ribs protruding radially outward towards the central axis. The proximal end of the inner sidewall may have one or more inwardly protruding tabs. The device may also comprise a needleless IV connector disposed in the open central cavity of the inner sidewall and held between the one or more inwardly protruding tabs of the inner sidewall. The device may also comprise a keying element comprising a housing having a sidewall having a curved shape with a flat ledge on a top portion, the sidewall may have an open distal end and a proximal end may have a back wall. One or more detachable protrusions may extend radially outward along an outer circumference of the curved portion of the sidewall. The back wall may have an open central cavity. The one or more detachable interference ribs of the locking element may be configurable to form gaps in a pattern to correspond with an individual patient and the detachable protrusions of the keying element being configurable to complement the gaps formed on the locking element. The sidewall of the keying element may have a diameter smaller than the diameter of the outer sidewall of the locking element to enable the keying element to slide into the locking element when the gaps of the locking element are aligned with the protrusions of the keying element.

In one or more embodiments, the locking element may be placed on a drug delivery device and the keying element may be placed on an intravenous access device. In one or more embodiment, the drug delivery device may be a syringe. In one or more embodiments, the housing of the locking element may be imprinted with numerical values assigned to different detachable interference ribs and the housing of the keying element may be imprinted with numerical values assigned to different detachable protrusions.

The position of the protrusions on the keying element may be patient specific, specific to a route of administration or specific to a drug class. The device may also include a visual indicator for drug family identification.

BRIEF DESCRIPTION OF THE DRAWINGS

FIG. 2 shows one embodiment of the keying element of the drug delivery safety device of the present invention;

FIG. 3 shows one embodiment of a rotatable keying element of the drug delivery safety device of the present invention;

FIG. 4 shows an exemplary embodiments of various notch designs of the locking element;

FIG. 6 shows one embodiment of the rotary adjustment bench tool of the drug delivery safety device of the present invention;

FIG. 7 shows another embodiment of the rotary adjustment bench tool of the drug delivery safety device of the present invention;

FIG. 9 shows one embodiment of the cut adjusted keying system of the drug delivery safety device of the present invention;

FIG. 12 shows another embodiment of the cutter for a cut adjusted keying system of the drug delivery safety device of the present invention.

DETAILED DESCRIPTION

Before describing several exemplary embodiments of the invention, it is to be understood that the invention is not limited to the details of construction or process steps set forth in the following description and drawings. The invention is capable of other embodiments and of being practiced or carried out in various ways. Additionally, in the following, items which are substantially the same across the various embodiments are given the same reference numbers.

In general, the present invention describes a passive safety device that creates a lock and key mechanism between a syringe, intravenous catheter connector, IV bag spike, or point of interconnection in an IV administration set and the point of IV access (e.g., BD Q-Syte™ Luer Access Split Septum). It is envisioned that the lock mechanism is "configured" or "cut" at the pharmacy, or where IV medications (e.g., syringes, bags, lines for pumps), or fluid source, are prepared. The lock is part of the fluid source. The terms "configured" or "configurable" are defined as elements or mechanisms that may be removed, moved, rotated, reshaped, melted, repositioned, uncovered, or punctured.

Cut Flange

Figure 1:
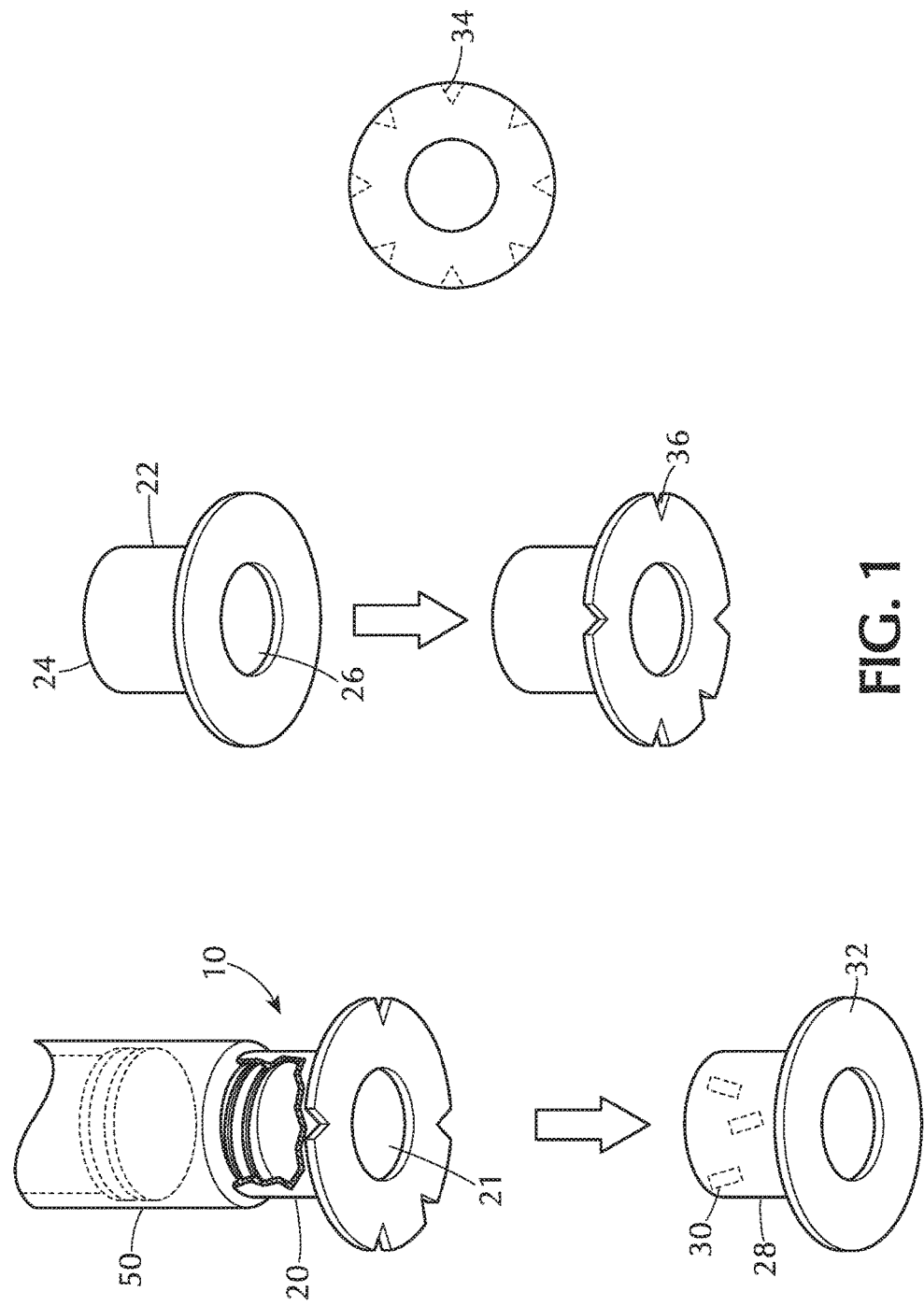
FIG. 1 shows one embodiment of the locking element of the drug delivery safety device of the present invention.

In one embodiment, as shown in FIG. 1, a drug delivery safety device 10 is provided having a locking element 20 having a body 22 with an open proximal end 24 and an open distal end 26, a sidewall 28 extending from the open proximal end to the open distal end, the proximal end of the sidewall having one or more adherence element 30 to attach the drug safety device to a drug delivery device 50, e.g. a syringe, intravenous catheter connector, IV bag spike, or point of interconnection in an IV administration set. Adherence element 30 may comprise any method of adherence known to a person of skill in the art, including but not limited to, interference fit, adhesives, locking tab, an indentation to attach the locking mechanism, or an integral or molded part to attach the drug safety device to a drug delivery device. As shown in FIG. 1, the one or more adherence elements 30 prevent removal of the safety device from the drug delivery device after the locking element has been attached to the drug delivery device. The distal end having at least one flange 32 with a plurality of mechanically configurable sections 344 to provide a plurality of openings or notches 36 in a receiving pattern. In one or more embodiments, mechanically configurable sections 34 may be in the form of cutouts. Configurable notches are defined as notches that may be removed, moved, rotated, reshaped, melted, repositioned, uncovered, or punctured. In one or more embodiments, a set of configurable notches or openings can be cut into the periphery of the flange of the locking element in a particular pattern that match the corresponding keying element. FIG. 1 shows a flange having pre-scored notches which may be selectively removed, moved, rotated, reshaped, melted, repositioned, uncovered, or punctured to provide a desired pattern of notches or openings.

In one embodiment, as shown in FIG. 2, a keying element 40 having a proximal end 42 and distal end 44, said proximal end 42 attachable to a vascular access device 48, and the distal end 44 having a flange with a plurality of configurable engagements members 46 to provide a complementary fit with the receiving pattern of the locking element. In one or more embodiments, the configurable engagement members may be in the form of projecting tabs. The flange with a plurality of configurable engagements members surround the intravenous access port. FIG. 2 shows the IV access key, starting from a blank keying element having a full set of configurable engagements members 46 for coding patient identification, application or drug type, or access points to a specifically keyed device wherein a sequence of engagements members or projecting tabs have been selectively configured to provide a complementary fit with a receiving pattern of a corresponding locking element.

In one or more embodiments, either the distal end of the locking element or the proximal end of the keying element have a plurality of mechanically configurable sections or cutouts to provide a plurality of notches or openings in a receiving pattern, and the corresponding distal end of the locking element or proximal end of the connector have a plurality of configurable engagements members or projection tabs to provide a complementary fit with the receiving pattern. In one or more embodiments, the locking element is applied to the IV access device, and the keying element is applied to the drug delivery device. In one or more embodiments, the keying element is applied to the IV access device, and the locking element is applied to the drug delivery device.

For illustration, the locking element 20 is shown in FIG. 1 attached to a syringe barrel serving as a drug delivery device 50.

The sidewall 28 of the locking element is coaxially disposed around the medical delivery device 50 and extends toward the open distal end of the medical delivery device. The distally extending sidewall defines an annular space 21 between the distally extending wall and the medical delivery device. In one or more embodiments, the annular space is configured or shaped to receive a keyed luer access device 60. In one or more alternative embodiments, the distally extending wall is shaped or configured to engage the keyed luer access device. In the embodiments shown in FIG. 1, the distally extending sidewall 22 includes an inside surface which is shaped to form a fluid-tight engagement with the IV access device.

The locking element 20, including the distally extending sidewall and the annular space, attached to the medical delivery device is shaped to prevent attachment of the medical delivery device to an unintended or incompatible IV access component or other device, including standard IV route-accessing devices, including, without limitation, blunt cannula split-septum, luer access mechanical valves, luer access mechanical valves with positive displacement, luer access split-septa.

FIG. 3 shows an exemplary design of a rotating keying element wherein the plurality of configurable projection tabs are provided on a flange 60 having a central opening 62. An elastomeric ring 64 may placed in the central opening. The flange 60 is subsequently inserted into a groove formed in the body of the intravenous access device 44. The rotating keying element allows for the use of the locking threads of the Luer connection. Specifically, the rotating keying element allows for insertion of the keying element into the locking element, while permitting conventional function of the Luer lock by rotating the syringe or interconnection. The flange may be spring loaded with a spring wire to return the keying element to a desired starting position.

FIG. 4 shows exemplary keying elements with a variety of notch designs which may be utilized to distinguish between different types of intravenous applications, for example, standard IV, chemotherapy and anesthesia. In one or more embodiments, various shapes, e.g. rectangular, may be used to distinguish different drug classes to provide the advantage of being able to utilize the same patient code and corresponding lock and key cutting devices, while adding additional protection for different administration sites.

In one or more embodiments, the locking element preferably has metal locking tabs that are angled into, and point towards the drug delivery device, e.g. syringe barrel, that prevent removal once applied. Many options exist to prevent removal of the drug delivery safety device from the drug delivery device, including adhesives, plastic features, etc. The open distal end of the drug delivery device, e.g. syringe tip, is disposed within the cylindrical portion of the locking element to prevent bypassing the lock. Other lock and key designs could also be employed besides flange-like designs. For example, it is envisioned that the adherence elements may be disposed on an internal or external wall of a cylinder or other shape device. Many lock designs can be imagined that would prevent an interconnection, but the most important feature is the ability to code the interconnection between the locking element and the keying element. If the lock and key are not complementary, then the health care provider will not be able to insert the fluid source into the IV access site. This decreases the chances that a patient will receive drugs intended for another patient. Although the system can be utilized with any fluid interconnection system, the primary application would allow the continued use of the Luer lock, but add a safety lockout feature to the system. In one or more embodiments, lock and keying methods that prevent or brake the syringe plunger from being depressed are also contemplated. However, these mechanisms are not preferred due to the large variation in plunger dimensions.

It is desirable to minimize the likelihood of forced interconnection. The term coding scheme is the method by which locks are keyed to specific patients, drug families, or access points. This is implemented by selecting locations of tabs and notches, their shapes, and the algorithm used to cut them. If improper coding schemes are selected, it can be imagined that situations exist where there might only be one projection tab blocking the connection. Therefore, any scheme selected should allow for sufficient projection tabs on the keying element to block the interconnection with the notch on the locking element.

In one or more embodiments, three or more projection tabs are always distributed around the flange of the keying element. The shape of the flanges can be selected to more easily indicate how the lock and key should be aligned. This can be through shape selection (e.g., "D-shape") or adding features like notches, colors, or other indicators of proper alignment. The locking element may be in various shapes, including but not limited to, cylindrical, rectangular, triangular, etc. The flange of the locking element may also be in various shapes, including but not limited to, circular, rectangular, triangular, etc. Keying tabs and corresponding notch features can have various incompatible shapes (pie slice shapes are shown, as well as rectangular shapes, but any set of mutually locking shapes can be employed). Key tabs and corresponding notch features can be on the periphery or anywhere within the flange. The key tabs and corresponding notch features can also be multi-layered, in the case where there would be more than one flange which can further prevent forced connections.

In one or more embodiments, a simple coding scheme would allow for an assignment of a code to the last two digits of the patients ID, or social security number. This would reduce the risk of misadministration assuming these two digits are randomly distributed in the hospital. Many other coding schemes are envisioned, as are known in the field of information theory.

In one or more embodiments, the lock and key may also be color coded to identify drug families, such as anesthesia drugs, chemotherapy, or antibiotics. These colors would provide visual reminders as well as matching drug class keys.

The drug delivery safety device of the present invention can be implemented either as a mandatory lock or as an added safety feature, depending on the clinical environment and specific needs. In mandatory lock situations, all non-lock devices cannot contact the IV access device. In one embodiment of mandatory lock mode, a locking element can be implemented where only one corresponding keying element prevents access to the drug delivery device. In the case of the mandatory locking scheme, a universal or master keying element can be designed that deactivates the locking element without being specifically keyed for a patient. This would allow for rapid access in clinical situations where time is of the essence. In added safety situations, conventional devices can still contact the access device, for example in the case of emergency, or if a drug dose comes from an area of the hospital that is not participating in the locking system. However, the system still provides added safety for doses coming from sources that are using the locking technology.

Lock and key cutting equipment, as well as interconnections with hospital information technology systems to ensure and automate proper coding is also contemplated.

In another embodiment of the present invention, a locking element notch cutter (not shown) and keying element tab cutter (not shown) is provided. The lock and key cutters would be used to customize blanks (e.g., no notches cut, no tabs removed) to make them patient specific. The lock cutter could be used as a step in drug preparation process in the pharmacy, for example. The key cutter would be employed by the IV team or floor nurse for the patient side of the circuit. These systems could range from purely mechanical, to automated, integrated systems that link to other patient, data, care management systems.

In one or more embodiments, one or more sensors may be placed on the locking element and keying element that detect interconnections and report these to another information system for automated medical records or monitoring purposes. Sensors could also detect stress and strain, indicating improper forced connections, or even incorrect connections that were prevented.

In one or more embodiments, the keying element may be prepared by the patients' care providers, or the IV team. In one or more embodiments, the locking element may be prepared by the pharmacy.

Rotary-Adjustable Key and Keyway

Figure 5:
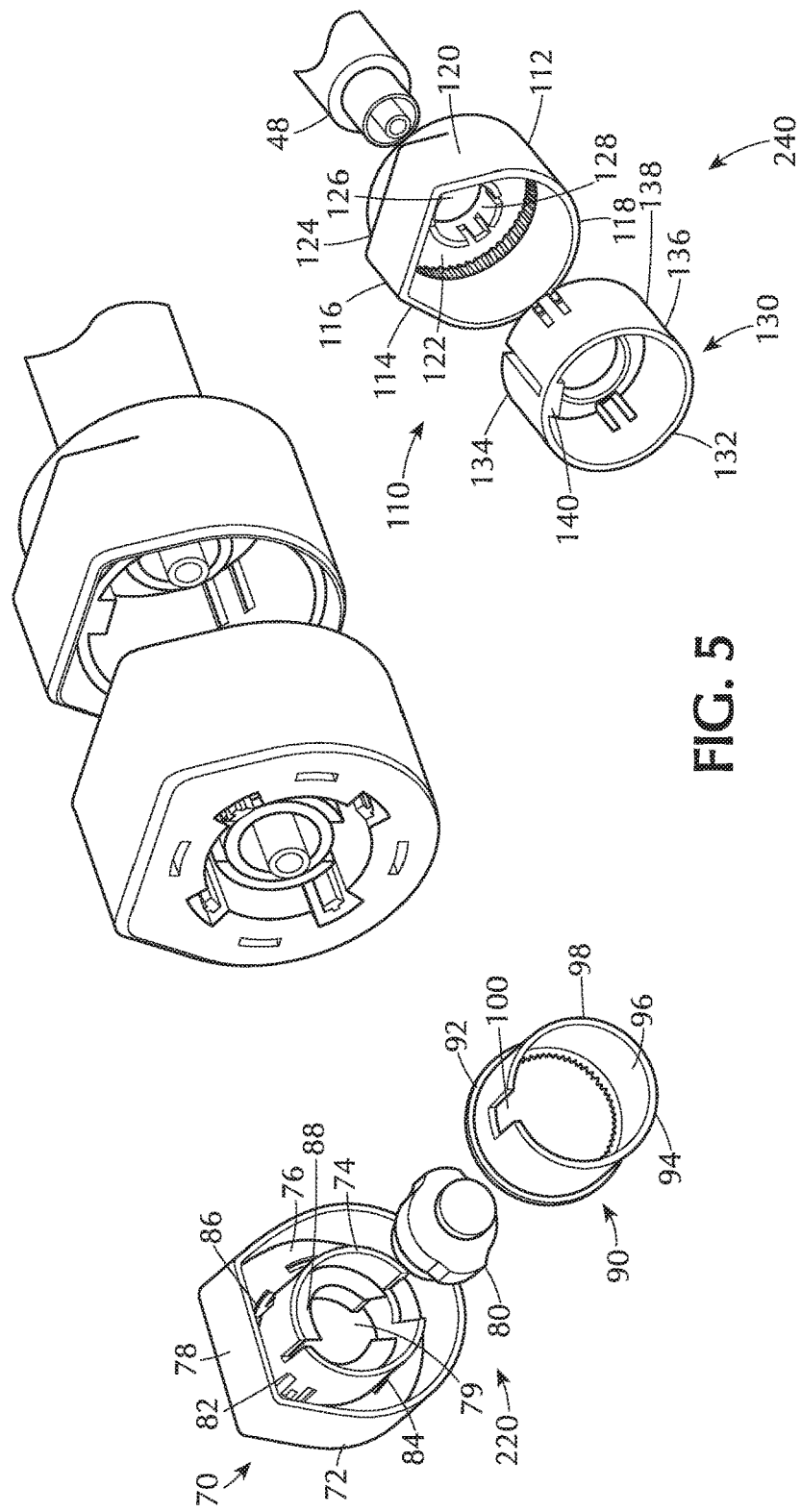
FIG. 5 shows one embodiment of the rotary adjusted keying system of the drug delivery safety device of the present invention.

In another embodiment of the present invention, as shown in FIG. 5, a drug delivery safety device 10 is provided comprising a locking element 220 having a housing 70 having an outer sidewall 72, an inner sidewall 74, a back wall 76 located between the inner and outer sidewalls. The outer sidewall 72 has a curved shape with a flat ledge on a top portion 78. The inner sidewall 72 creates an open central cavity 79 to house a needleless IV connector 80 e.g. a luer access split septum stand alone device. The inner sidewall has a distal end 82 and a proximal end 84, the distal end having one or more detenting ribs 86 protruding radially outward from the central axis located around the outer circumference. The proximal end 84 of the inner sidewall has one or more inwardly protruding tabs 88. A needleless IV connector may be disposed in the open central cavity 79 of the inner sidewall and held between the one or more inwardly protruding tabs 88 of the inner sidewall. A first insert 90 has an open distal end 92 and an open proximal end 94, along with a sidewall 96 that extends between the open distal end 92 and the open proximal end 94. The sidewall 96 on the distal end includes one or more detents 98 on an inside circumference of the sidewall 96 protruding radially inward toward the central axis. The one or more detents 98 of the first insert 90 has a complimentary fit with the one or more detenting ribs 86 of the housing when the insert is place into the housing. A keyway 100 is cut into the sidewall 96 on the proximal end 94.

The drug delivery safety device 10 further includes a keying element 110 comprising a housing 112 having a outer sidewall 114 having a curved shape with a flat ledge 116 on a top portion. The outer sidewall 114 has an open distal end 118 and a proximal end 120 having a back wall 122. An inside surface of the proximal end of the outer sidewall having one or more detents 124 protruding radially outward from the central axis located around the circumference of the inside surface of the proximal end of the outer sidewall. The back wall 122 includes an open central cavity 126 formed by a second inner wall 128 to house a second insert 130.

The second insert 130 includes an open distal end 132, an open proximal end 134 and a sidewall 136 extending between the open distal end and the open proximal end. The sidewall 136 on the proximal end having one or more detenting ribs 138 on an outer circumference of the sidewall protruding radially outward. The one or more detenting ribs 138 of the insert have a complimentary fit with the one or more detents 124 of the housing when the insert is place into the housing. A key tab 140 projects radially inward from the distal end of the second insert toward the central axis. The outer sidewall of the keying element having a diameter smaller than the outer diameter of the outer sidewall of the locking element 220 to enable the keying element to slide into the locking element 220 when the keyway of the locking element is aligned with the tab projecting radially inward from the distal end of the second insert.

The keyway 100 on the locking element and the tab 140 projecting radially inward from the distal end of the second insert of the keying element are aligned to one another by rotating the keyway or tab into position prior to sliding the locking element and keying element so that the detenting ribs (86, 138) engage the corresponding detents (98, 124). Each individual patient is assigned a specific positioning for the keyway 100 of the locking element and the protruding tab on the keying element.

With the keyway and key tab being freely rotatable within the housing, an infinite number of relative positions of angular adjustment are afforded. Once the keyway and key tabs are rotationally adjusted into a complementary pattern, the inserts can be fixed in a selected position of adjustment and maintained by fixing the detents on to the detenting ribs of the corresponding locking element and keying element.

Upon assembly, the needleless IV connector 80 is positioned into the open central cavity 79 of the inner sidewall of the locking element 220 and inserted into the central cavity until the needleless IV connector 80 is disposed in the open central cavity of the inner sidewall and held between the one or more inwardly protruding tabs 88 of the inner sidewall of the locking element. The keyway 100 of the locking element is rotated into a specific position that has been assigned to the individual patient and the first insert 90 is then inserted into the housing of the locking element so that one or more detents 98 of the sidewall on the distal end on an inside circumference of the sidewall protruding radially inward toward the central axis engages the one or more detenting ribs 86 of the housing when the insert is place into the housing in a complimentary fit. The locking element 220 is now assembled. The locking element is placed onto a drug delivery device or fluid container to restrict access to the drug delivery device or fluid container.

Similarly the protruding key tab 140 of the keying element is rotated into a specific position that corresponds with the keyway 100 of the locking element assigned to the individual patient. Once the protruding tab 140 of the keying element is rotated into the specific assigned position, the second insert 130 is then placed into the housing of the keying element so that the one or more detenting ribs 138 of the second insert 130 engage the one or more detents 124 of the housing of the keying element in a complimentary fit. The keying element is now assembled. The keying element is placed onto an IV access device on the patient.

Figure 8:
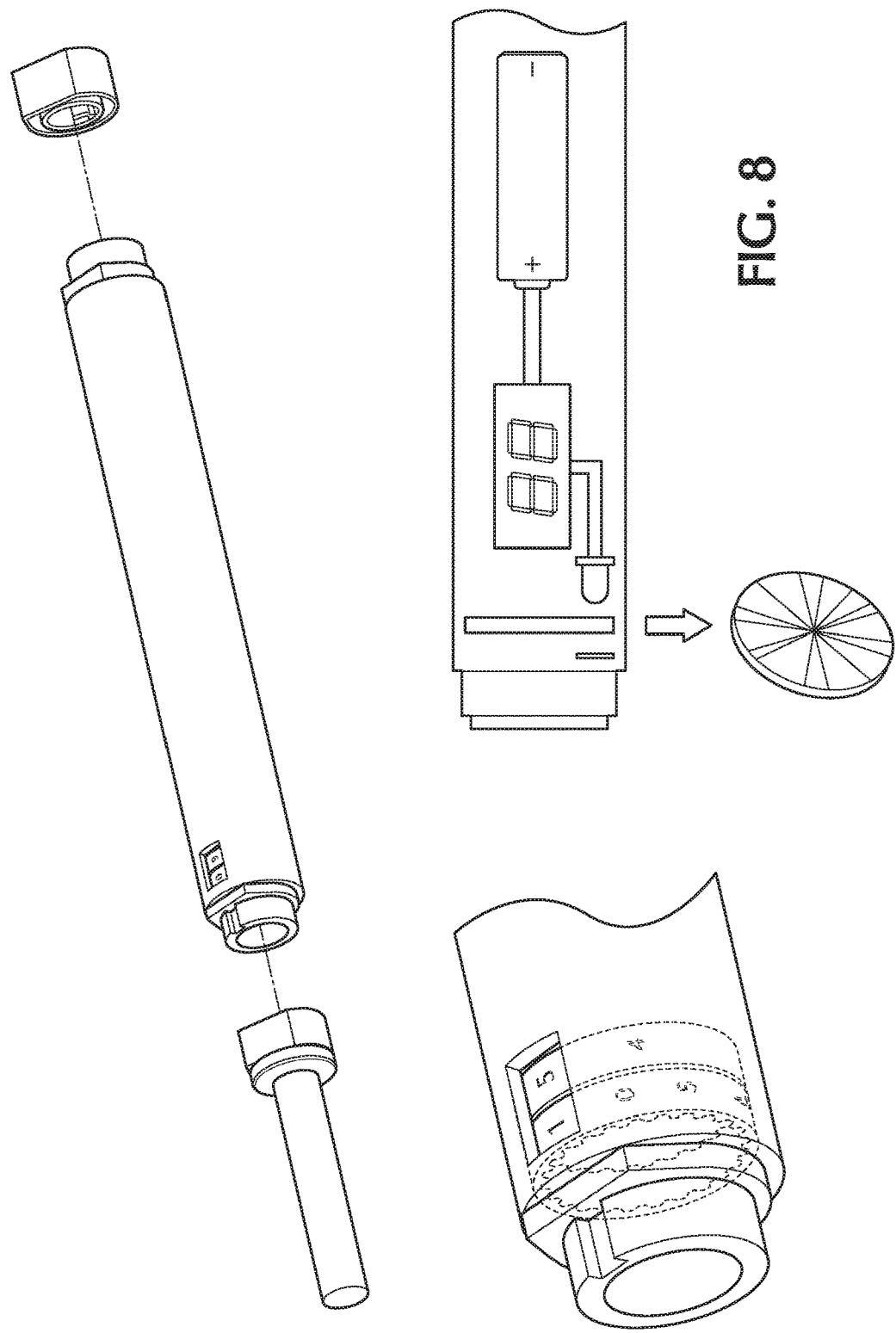
FIG. 8 shows yet another embodiment of the rotary adjustment tool of the drug delivery safety device of the present invention.

In one more embodiments, as shown in FIGS. 6 and 7, the protruding key tab of the keying element and the keyway of the locking element may be rotated into a specific position that corresponds with assigned to the individual patient using a bench top tool 110 designed to provide torque to rotate the key tab or keyway into a specific position. As shown in FIGS. 6 and 7, in one or more embodiments, the outer surface of the locking element or keying element that comprises a base plane 120. Extending from a central region of the base plane 140 is a stem 142. The stem 142 has at least one face so that it can impart torque to adjust the keyway or key tab. The cross-sectional shape of the stem 142 may be, for example, hexagonal, rectangular, star-shaped, etc., with respect to the base plane 140. As shown in FIG. 7, the position may be assigned a numerical value 120 that may be imprinted in the outside surface of the outer housing of the locking element and keying element so that it is visible to the pharmacist and the medical care provider. In another embodiment, as shown in FIG. 8, the protruding key tab of the keying element and the keyway of the locking element may be rotated into a specific position that corresponds with assigned to the individual patient using a handheld rotary adjustment tool having a mechanical or optical gear counter wherein the tool comprises two or more gears to adjust the position of the keyway and corresponding key tab.

To deliver medication from the drug delivery device into the IV access device on the patient, the flat ledge 78 on a top portion of the locking element is aligned with the flat ledge 116 on a top portion of the keying device. If the proper locking element 220 is delivered to the patient, the keyway 100 of the locking element will also align with the protruding key tab 140 of the keying element allowing the locking element 20 to properly engage the keying element 240 so the IV access device 48 engages the needleless IV connector 80 of the locking element thus allowing medication to flow from the drug delivery device to the patient. However if the proper locking element is not delivered to the patient, the keyway 100 of the locking element will not align properly with the protruding key tab 140 of the keying element thus preventing the locking element 220 to properly engage the keying element 40, thereby preventing the IV access device 48 to engages the needleless IV connector 80 of the locking element thus preventing medication to flow from the drug delivery device to the patient. Thus, the locking element is "keyed" to the complementary keying element by adjusting the radial orientation of keyway on the locking element placed on the drug delivery device to correspond with the radial orientation of the key tab on the keying element placed on the patient's IV access device.

Each patient is provided a respective locking element and keying element that is unique to that patient. In one or more embodiments, the keying element may be physically associated with or affixed to the patient's IV access device. The keying element may be provided to the patient with the identification bracelet.

An exemplary use of the safety device system is described as follows. First, a health care provider determines that a specific type and dosage of medication is required to be administered to the patient. A prescription for this medication is sent to the pharmacy, which then works to fill the order. The pharmacy is provided with the keying information assigned to the individual patient. The keyway 100 on the locking element is adjusted at the pharmacy to correspond to the key tab 140 of the keying element assigned to the individual patient. The locking element is then placed onto the drug delivery device or fluid container to prevent access to the medication within the container or device by a non-complimentary patient keying element. Thereafter, the device or container can only be accessed by the key tab 140 or a master key by the health care provider at the time of administration to the patient. Access to the medication within the drug delivery device or container is thereby restricted.

The pharmacy provides the drug delivery device or container having the locking element to the health care provider, who then physically brings the access restricted drug delivery device or container to the patient. In one or more embodiments, the health care provider may adjust the keying element on the patient's IV access device to correspond to the keyway on the locking element as adjusted at the pharmacy using a rotary adjustment tool as described further in this application. Once the keyway on the fluid container is aligned with the key of the patient's IV access device, the medication within the container may be accessed and administered to the patient.

In one or more embodiments, only the patient's keying element may be used to access the locking element on the fluid container. Such restrictive access, however, may prove inconvenient or even dangerous if the keying element is unavailable for a variety of reasons. For example, if the access restricted fluid container is brought to the patient and the key cannot be accessed or has been discarded for some reason, then neither the patient nor the health care provider will be able to access the medication. Alternatively, in medical emergencies, the keying element may not be readily at hand when time is at a premium. As a result, in another embodiment of the present invention, a master keying element that is capable of unlocking all classes of locking element may be provided or given to any suitable member of the health care provider team.

Although the above embodiments are illustrated utilizing a limited number of keyways and corresponding key tab, it should be clear that any number of keyways and corresponding key tabs may be employed. Moreover, although the above embodiments provide a single unique key to each patient, such a strict one-to-one correlation is not necessarily required.

Rotary-Cut

In yet another embodiment of the present invention, as shown in FIG. 9, a drug delivery safety device is provided comprising a locking element 320 having a housing having an outer sidewall 160, an inner sidewall 162, a back wall 164 located between the inner and outer sidewalls; the outer sidewall 162 having a curved shape with a flat ledge 166 on a top portion, the inner sidewall creating an open central cavity 168 to house a needleless IV connector 180 e.g. a luer access split septum stand alone device. The inner sidewall 162 having a distal end 170 and a proximal end 172, the circumference of the inside surface of the curved portion of the outer sidewall having one or more detachable interference ribs 176 protruding radially outward towards the central axis located around the outer circumference, the proximal end of the inner sidewall having one or more inwardly protruding tabs 178. A needleless IV connector 180 is disposed in the open central cavity 168 of the inner sidewall and held between the one or more inwardly protruding tabs 178 of the inner sidewall.

A keying element 340 includes a housing having a sidewall 342 having a curved shape with a flat ledge 344 on a top portion, the sidewall 342 having an open distal end 346 and a proximal end 348 having a back wall 350. One or more detachable protrusions 352 extend radially outward along an outer circumference of the curved portion of the sidewall. The back wall 350 includes an open central cavity 354.

Figure 10:
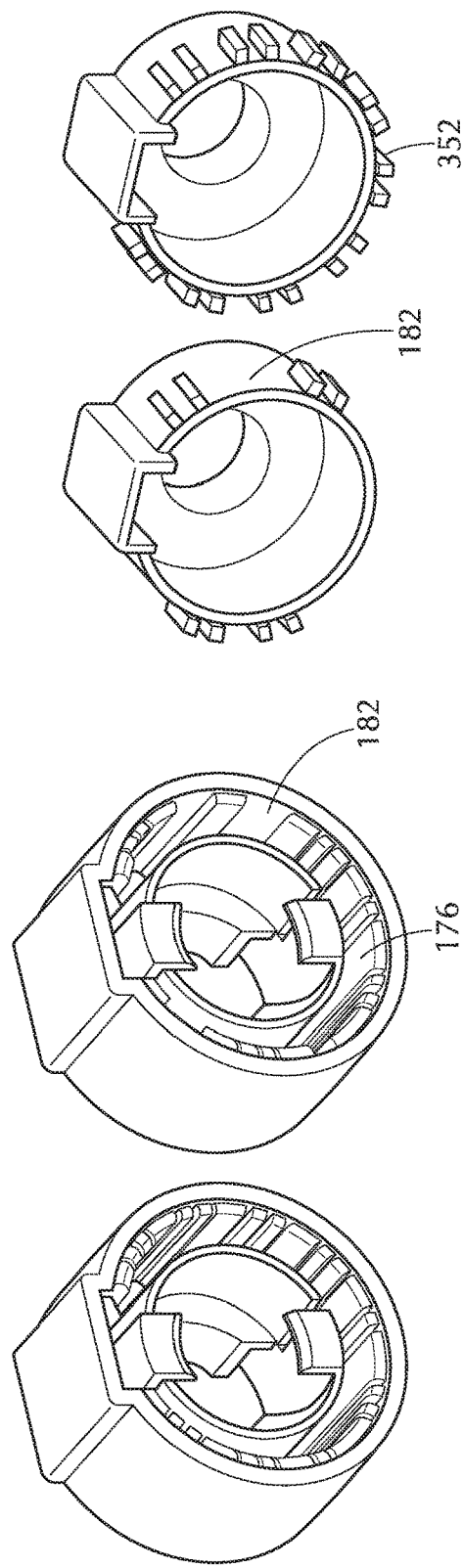
FIG. 10 shows one embodiment of the locking element and keying element of the cut adjusted keying system of the drug delivery safety device of the present invention.

As shown in FIG. 10, the one or more detachable interference ribs 176 of the locking element may be selectively configured to form gaps 178 in a pattern to correspond with an individual patient and the detachable protrusions of the keying element being selectively configured to complement the gaps 182 formed on the locking element.

The sidewall of the keying element 340 has a diameter smaller than the diameter of the outer sidewall of the locking element 320 to enable the keying element to slide into the locking element when the flat ledge 166 on a top portion and gaps 178 of the locking element are aligned with the flat ledge 344 and protrusions 352 of the keying element.

Each individual patient is assigned a specific positioning for the gaps 178 formed between the detachable interference ribs 176 of the locking element and the protrusions 352 on the keying element. It may be desirable to design unique corresponding patterns of protrusions and depressions, so that each locking element is unique to every other keying element. It may also be desirable to provide at least two protrusions that are unique to each keying element.

Upon assembly, the needleless IV connector 180 is positioned into the open central cavity 168 of the inner sidewall of the locking element and inserted into the central cavity until the needleless IV connector is disposed in the open central cavity of the inner sidewall and held between the one or more inwardly protruding tabs 178 of the inner sidewall of the locking element. The detachable interference ribs 176 of the locking element are configured to form a specific pattern of gaps that has been assigned to the individual patient. The locking element 320 is now assembled. The locking element 320 is placed onto a drug delivery device or fluid container.

Similarly the detachable protrusions 352 of the keying element are configured to form a complementary pattern that corresponds with the specific pattern of gaps formed on the locking element that is assigned to the individual patient. The keying element 340 is now ready to be placed onto an IV access device on the patient.

The detachable interference ribs of the locking element and the detachable protrusions of the keying element may be assigned a numerical value that may be imprinted in the outside surface of the outer housing of the locking element and keying element so that it is visible to the pharmacist and the medical care provider.

To deliver medication from the drug delivery device into the IV access device on the patient, the flat ledge 166 on a top portion of the locking element 320 is aligned with the flat ledge 344 on a top portion of the keying element 340. If the proper locking element 320 is delivered to the patient, the specific pattern of gaps 182 formed on the locking element 320 by removing a specific sequence of interference ribs 176 will also align with the complementary pattern of protrusions 352 of the keying element 340 allowing the locking element 320 to properly engage the keying element 340 so the IV access device engages the needleless IV connector 180 of the locking element thus allowing medication to flow from the drug delivery device to the patient. However if the proper locking element 320 is not delivered to the patient, the specific pattern of gaps 182 formed on the locking element will not align properly with the protrusions 352 of the keying element thus preventing the locking element 320 to properly engage the keying element 340, thereby preventing the IV access device to engages the needleless IV connector of the locking element thus preventing medication to flow from the drug delivery device to the patient.

When medication is to be prescribed to the patient, the doctor places an order with the pharmacy regarding the type of medication to be delivered to the patient. The pharmacy fills the order and configures a locking element 320 to the corresponding patient by removing or cutting the sequence of interference ribs 176 on the locking element to correspond to the depressions 182 formed by removing a particular sequence of protrusions 352 in the corresponding keying element.

In one or more embodiments, if an emergency exists, a master keying element may be used to unlock keying element 340.

In one or more embodiments, the present invention allows for keying not only per patient but per application. Keying can also be coded to be drug-family specific. The drug delivery safety device and system described in the present invention can be added to off-the-shelf drug delivery devices and IV access devices. The drug delivery safety device and system described in the present invention can also be added to syringes and IV access devices at the time of manufacture, which simplifies and reinforces their use in the clinical setting.

Cutter

Figure 11:
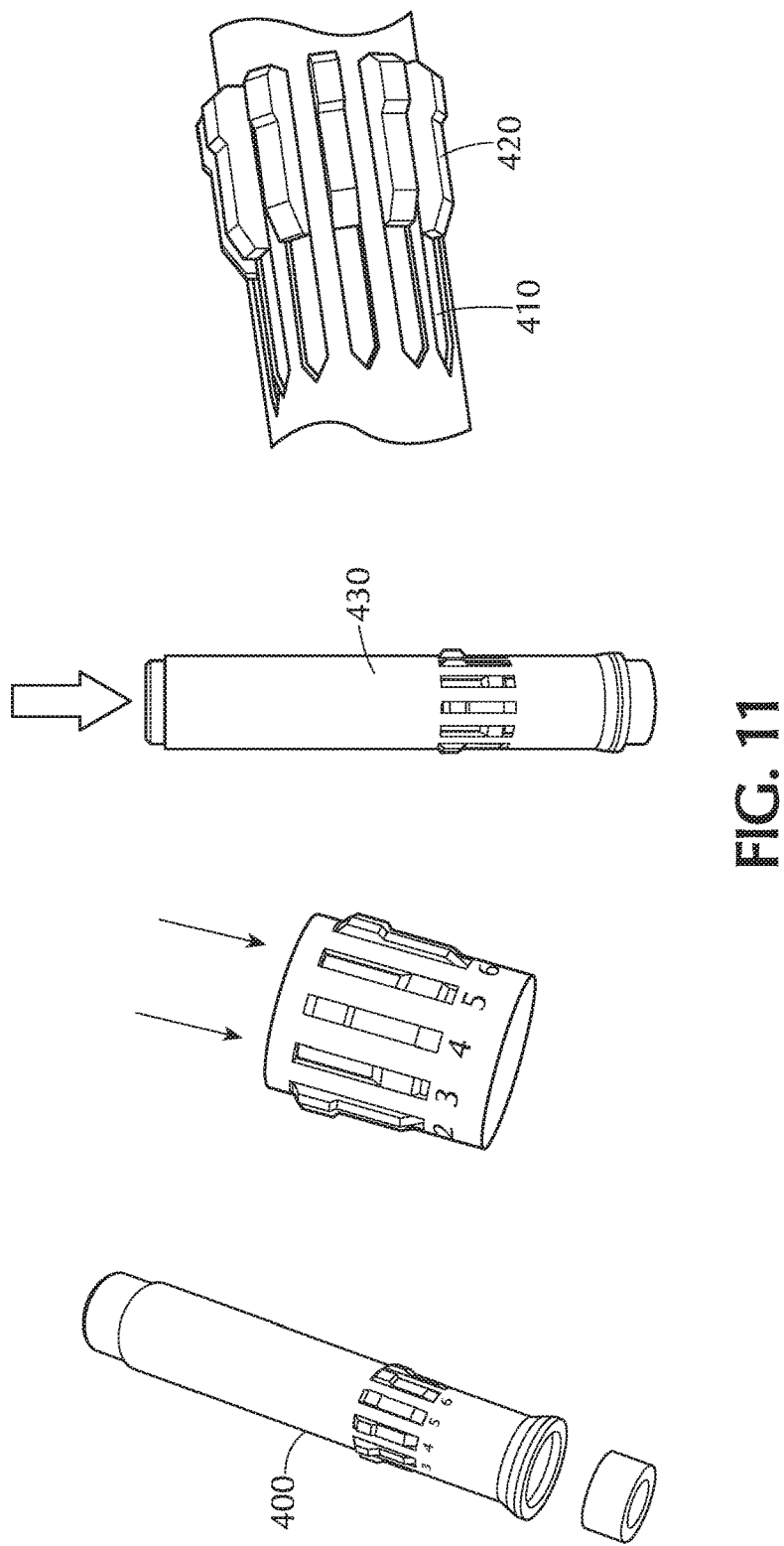
FIG. 11 shows one embodiment of the cutter for a cut adjusted keying system of the drug delivery safety device of the present invention.

In another embodiment of the present invention, as shown in FIGS. 11 and 12, a cutter 400 containing multiple blades 410 affixed to different levers 420 housed in a cutter body 430. The blades 410 can be optionally selected for use readily using a slidable lever 420 or turnable knob 440 having a projected edge in cam contact with the top end of the blade-affixed levers. The top end of the desired blade-affixed lever 420 is pushed downward for use, or in an alternate embodiment, the turnable knob 440 is rotated, so to enable a person to select a desired blade quickly and readily. The hollow interior of said cutter body 430 is filled with numerous blade-affixed levers. A spring may be compressed in the body for allowing the blade-affixed lever to project out of the distal end of said cutter body for use. The multiple blade-affixed lever are separated from each other to allow a user to freely select different blades. Each lever/projection may be individually numbered to allow the user to select the proper sequence/pattern of blades to configure the corresponding ribs to create the unique keying code.

Referring to FIG. 12, the multiple blade-affixed lever 460 disposed in the cutter body are in a releasing relationship with the turnable knob 440. When the turnable knob 440 is rotated, the desired blade-affixed lever 460 begins to come into contact with a cam which gradually moves the blade-affixed lever downward until the blade projects forward in the body and into a position to allow the blade to cut a desired protrusion or interference rib from a locking element or keying element. The turnable knob 440 has its outer surface denticulated for easy operation of the knob without slipping as shown in FIG. 12.

When the cutter is not in use, the turnable knob is turned to release the downwardly pushed lever/projection to move out of the open distal end and retract into the cutter body along with the lever/projection.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A drug delivery safety device comprising:
a locking element comprises a housing having a curved-shaped outer sidewall with a flat ledge on a top portion, an inner sidewall having an open central cavity, a back wall located between the inner and outer sidewalls;
the inner sidewall having a distal end and a proximal end, the distal end having one or more detenting ribs protruding radially outward around the outer circumference, the proximal end of the inner sidewall having one or more inwardly protruding tabs;
a needleless IV connector disposed in the open central cavity of the inner sidewall and held between the one or more inwardly protruding tabs of the inner sidewall;
a first insert having an open distal end and an open proximal end; a sidewall extending between the open distal end and the open proximal end, the sidewall on the distal end having more than one detents on an inside circumference of the sidewall protruding radially inward toward the central axis, the one or more detents of the first insert having a complimentary fit with the one or more detenting ribs of the housing when the first insert is place into the housing;
a keyway cut into the sidewall on the proximal end of the first insert to correspond with an individual patient;
a keying element comprising a housing having a outer sidewall having a curved shape with a flat ledge on a top portion, the outer sidewall having an open distal end and a proximal end having a back wall, an inside surface of the proximal end of the outer sidewall having one or more detents located around the circumference of the inside surface of the proximal end of the outer sidewall protruding radially outward, the back wall having an open central cavity formed by a second inner wall;
a second insert having an open distal end and an open proximal end; a sidewall extending between the open distal end and the open proximal end, the sidewall on the proximal end having one or more detenting ribs on an outer circumference of the sidewall protruding radially outward, the one or more detenting ribs of the second insert having a complimentary fit with the one or more detent of the housing when the second insert is place into the housing, a key tab projecting radially inward from the distal end of the second insert toward the central axis;
the outer sidewall of the keying element having a diameter smaller than the outer diameter of the outer sidewall of the locking element to enable the keying element to slide into the locking element when the keyway of the locking element is aligned with the tab projecting radially inward from the distal end of the second insert.

2. The drug delivery safety device of claim 1 wherein the locking element is placed on a drug delivery device.

3. The drug delivery safety device of claim 2 wherein the drug delivery device is a syringe.

4. The drug delivery safety device of claim 1 wherein the keying element is placed on a intravenous access device.

5. The drug delivery safety device of claim 1 wherein the position of the keyway and key tab is patient specific.

6. The drug delivery safety device of claim 1 wherein the position of the keyway and key tab is specific to a route of administration.

7. The drug delivery safety device of claim 1 wherein the position of the keyway and key tab is specific to a drug class.

8. The drug delivery safety device of claim 1 further comprising a visual indicator for drug family identification.

9. The drug delivery safety device of claim 1 wherein the housing of the locking element is imprinted with numerical values assigned to different positions of the keyway.

10. The drug delivery safety device of claim 1 wherein the housing of the keying element is imprinted with numerical values assigned to different positions of the key tab.

11. The drug delivery safety device of claim 1 wherein the housing of the keying element is imprinted with numerical values assigned to different detachable protrusions.

* * * * *